United States Patent
Kakei et al.

(10) Patent No.: US 10,327,675 B2
(45) Date of Patent: Jun. 25, 2019

(54) MOTOR FUNCTION ANALYSIS SYSTEM AND OPERATIONAL METHOD OF SYSTEM

(71) Applicant: TOKYO METROPOLITAN INSTITUTE OF MEDICAL SCIENCE, Tokyo (JP)

(72) Inventors: Shinji Kakei, Tokyo (JP); Jongho Lee, Tokyo (JP); Satoshi Orimo, Tokyo (JP); Akira Inaba, Tokyo (JP); Yasuhiro Okada, Tokyo (JP)

(73) Assignee: TOKYO METROPOLITAN INSTITUTE OF MEDICAL SCIENCE, Tokyo (JP)

( * ) Notice: Subject to any disclaimer, the term of this patent is extended or adjusted under 35 U.S.C. 154(b) by 0 days.

(21) Appl. No.: 14/787,411

(22) PCT Filed: Apr. 30, 2014

(86) PCT No.: PCT/JP2014/061972
§ 371 (c)(1),
(2) Date: Oct. 27, 2015

(87) PCT Pub. No.: WO2014/178400
PCT Pub. Date: Nov. 6, 2014

(65) Prior Publication Data
US 2016/0073936 A1    Mar. 17, 2016

(30) Foreign Application Priority Data

Apr. 30, 2013 (JP) ................. 2013-095173

(51) Int. Cl.
*A61B 5/11* (2006.01)
*A61B 5/00* (2006.01)

(52) U.S. Cl.
CPC .......... *A61B 5/1124* (2013.01); *A61B 5/1101* (2013.01); *A61B 5/4064* (2013.01);
(Continued)

(58) Field of Classification Search
CPC ... A61B 5/1124; A61B 5/4064; A61B 5/7275; A61B 5/743; A61B 5/7257;
(Continued)

(56) References Cited

U.S. PATENT DOCUMENTS 8,660,641 B2 * 2/2014 Kakei ................. A61B 5/0488
600/546
8,792,977 B2 * 7/2014 Kakei ................. A61B 5/0488
600/546
(Continued)

FOREIGN PATENT DOCUMENTS

JP    2004016336 A    1/2004
JP    2004136074 A    5/2004
(Continued)

OTHER PUBLICATIONS

Duval, et al. "The Dynamic Relationship Between Voluntary and Involuntary Motor Behaviours in Patients with Basal Ganglia Disorders." The Basal Ganglia IX. Springer, New York, NY, 2009. 521-534.*

(Continued)

*Primary Examiner* — David J. McCrosky
(74) *Attorney, Agent, or Firm* — Meunier Carlin & Curfman LLC

(57) ABSTRACT

The present invention has an objective of evaluating a motor function of a subject with a neurodegenerative disease with high accuracy using a motor function analysis system that utilizes a wrist joint movement of the subject. The motor function analysis system includes: a display unit for displaying image information including a moving target image and a cursor image for tracking the target image; a moving unit used by the subject to move the cursor image; and an analyzer for detecting the tracking status of the target image (Continued)

tracked by the cursor image and analyzing the frequency of the movement components contained in the tracking status.

18 Claims, 9 Drawing Sheets

(52) U.S. Cl.
CPC .......... *A61B 5/4082* (2013.01); *A61B 5/7257* (2013.01); *A61B 5/7275* (2013.01); *A61B 5/743* (2013.01); *A61B 5/4842* (2013.01); *A61B 5/4848* (2013.01)

(58) Field of Classification Search
CPC ... A61B 5/1101; A61B 5/4082; A61B 5/4848; A61B 5/4842
See application file for complete search history.

(56) References Cited

U.S. PATENT DOCUMENTS

| | | |
|---|---|---|
| 2011/0137196 A1 | 6/2011 | Kakei et al. |
| 2011/0213267 A1 | 9/2011 | Kakei et al. |

FOREIGN PATENT DOCUMENTS

| | | |
|---|---|---|
| JP | 2008245917 A | 10/2008 |
| WO | 2013049156 A1 | 4/2013 |

OTHER PUBLICATIONS

Ravichandran, et al. "Nonparametric identification of the elbow joint stiffness under compliant loads." Engineering in Medicine and Biology Society, 2004. IEMBS'04. 26th Annual International Conference of the IEEE. vol. 2. IEEE, 2004.*

Internet Archive, Mathworks.com, Matlab documentation 2013.*

Wallisch, Pascal, et al. MATLAB for neuroscientists: an introduction to scientific computing in MATLAB. Academic Press, 2009. Ch 17.*

Halaki, Mark, Nicholas O'Dwyer, and Ian Cathers. "Systematic nonlinear relations between displacement amplitude and joint mechanics at the human wrist." Journal of biomechanics39.12 (2006): 2171-2182.*

Howard, Ian S., et al. "A modular planar robotic manipulandum with end-point torque control." Journal of neuroscience methods 181.2 (2009): 199-211.*

Extended European Search Report issued in Application No. 14792013.6, dated Jan. 20, 2017.

Liu, et al., "Effects of visual feedback on manual tracking and action tremor in Parkinson's disease", Exp Brain Res 129, 1999, 477-481.

Okumura, et al., "Analysis of the Voluntary Movement in Parkinson's Disease Using Visually Guided Tracking Method", Electroencephalography and Clinical Neurophysiology 87:2, 1993, S34.

International Search Report issued for PCT/JP2014/061972 dated Jul. 29, 2014 with English translation.

Japanese Office Action dated Jan. 9, 2018 to the corresponding Japanese patent application No. 2015-514865 with English translation.

Matsumoto, Y. 2007. Evaluation and Biofeedback Training of Tremors Using Accelerometers: Biofeedback Research. 34 (2), pp. 9-16 with partial English translation.

Matsumoto, Y. et al. 2001, Studies of evaluation of tremor diseases by frequency analysis on tremor acceleration waveforms, Research Report ofNagaoka University of Technology. 23, pp. 93-97 with English abstract.

* cited by examiner

MOTOR FUNCTION ANALYSIS SYSTEM AND OPERATIONAL METHOD OF SYSTEM

CROSS-REFERENCE TO RELATED APPLICATIONS

This application is a 35 USC 371 national phase of International Application No. PCT/JP2014/061972 filed Apr. 30, 2014, which claims priority to JP Patent Application No. 2013095173 filed Apr. 30, 2013, the contents of all of which are hereby incorporated by reference herein in their entirety.

TECHNICAL FIELD

The present invention relates to a motor function analysis system for a patient with a central nervous system disease such as a neurodegenerative disease, and a method for operating said system. More particularly, the present invention relates to a motor function analysis system for evaluating a pathological condition of a patient with Parkinson's disease or a patient with cerebral stroke with high accuracy, and a method for operating said system.

BACKGROUND ART

The present inventors constructed a motor function analysis system for analyzing a motor command from a subject using hand joint movements and electromyograms (Japanese Patent No. 5154558, corresponding to U.S. Pat. No. 8,792,977).

This system is a motor function evaluating system for evaluating a motor function of a subject, comprising: (a) means for displaying image information including a target image and a cursor image for tracking said target image (monitor); (b) means used by the subject to move the cursor image (wrist joint manipulandum); (c) means for detecting the tracking status of the target image tracked by the cursor image (computer); (d) means for detecting the status of the muscle action of the subject using means (b) above (surface myoelectric signal measuring device); (e) means for analyzing the tracking status detected by means (c) above and the muscle action status detected by means (d) above (computer); and (f) means for evaluating the motor function of the subject using the results of analysis obtained with means (e) above as an index (computer).

PRIOR ART DOCUMENT

Patent Document

Patent Document 1: Japanese Patent No. 5154558

SUMMARY OF THE INVENTION

Problems to be Solved by the Invention

In this system, the wrist joint movement is measured with a wrist joint manipulandum while the electromyogram is measured with a surface myoelectric signal measuring device so as to use them to evaluate the motor function of a subject. However, this requires the works to attach the electrode of the electromyogram to the patient and, if necessary, adjust the position thereof, which often requires for about 30 minutes of time. As a result, the burden on the patient and the practitioner of the examination in terms of time was not negligible.

Thus, the present invention has an objective of evaluating a motor function of a subject with a central nervous system disease with a motor function analysis system utilizing one measurement data (wrist joint position) acquired from a predetermined movement (wrist joint movement) of the subject.

Means for Solving the Problems

In order to solve the above-described problem, the present inventors have gone through intensive studies and succeeded in evaluating a pathological condition of a patient with a central nervous system disease with high accuracy by using a motor function analysis system that utilizes the wrist joint movement and the like of the subject to quantitatively measure the microsteps (fine stepwise movement or microvibration around 6 Hz (3-8 Hz)) found in the movement of the patient with the central nervous system disease such as a neurodegenerative disease (Parkinson's disease) or cerebral stroke without measuring the electromyogram, thereby accomplishing the present invention.

Thus, the present invention is as follows.

(1) A motor function analysis system for analyzing a motor function of a subject, comprising: a display unit for displaying image information including a moving target image and a cursor image for tracking said target image; a moving unit used by the subject to move the cursor image; and an analyzer for detecting the tracking status of the target image tracked by the cursor image and analyzing the frequency of the movement components contained in the tracking status.

(2) The system according to (1), wherein the analyzer separates the disease-induced movement component relevant to the disease of the subject from the non-disease-induced movement component irrelevant to the disease of the subject. (3) The system according to (2), wherein the disease-induced movement component is a movement component caused by a central nervous system disease of the subject. (4) The system according to either one of (2) and (3), wherein the disease is Parkinson's disease or cerebral stroke. (5) The system according to any one of (2) to (4), wherein a frequency range caused by the disease-induced movement component differs from a frequency range resulting from the frequency of the non-disease-induced movement component.

(6) The system according to any one of (2) to (5), wherein the frequency range caused by the disease-induced movement component is higher than the frequency range resulting from the frequency of the non-disease-induced movement component. (7) The system according to any one of (2) to (6), wherein the disease-induced movement component is a movement component relevant to involuntary movement of the subject. (8) The system according to any one of (2) to (7), wherein the non-disease-induced movement component is a movement component relevant to voluntary movement of the subject. (9) The system according to any one of (2) to (8), wherein the analyzer classifies, evaluates or quantifies the motor function of the subject according to the ratio of the quantity of the disease-induced movement component and the quantity of the non-disease-induced movement component. (10) The system according to any one of (2) to (9), wherein the disease-induced movement component is a movement component caused in voluntary movement of a patient with a central nervous system disease such as a patient with Parkinson's disease.

(11) The system according to any one of (2) to (10), wherein the non-disease-induced movement component contains a predicted movement component for moving the cursor image based on the subject's prediction of the movement of the target image, and a feedback movement component for the subject to correct the error between the target image and the cursor image. (12) The system according to (11), wherein the analyzer classifies, evaluates or quantifies the motor function of the subject according to the ratio of the quantity of the disease-induced movement component and the quantity of the predicted movement component. (13) The system according to any one of (1) to (12), wherein the frequency analysis is carried out using a Fourier analysis. (14) The system according to (13), wherein the Fourier analysis is a fast Fourier analysis.

(15) A method for operating a motor function analysis system for analyzing a motor function of a subject, comprising the steps of: displaying image information including a moving target image and a cursor image for tracking the target image on a display unit; moving the cursor image with a moving unit manipulated by the subject; and detecting the tracking status of the target image tracked by the cursor image and analyzing the frequency of the movement component contained in the tracking status with an analyzer. (16) The method according to (15), wherein, in the step for analyzing the frequency, the analyzer separates the disease-induced movement component relevant to the disease of the subject from the non-disease-induced movement component irrelevant to the disease of the subject. (17) The method according to (16), wherein the disease-induced movement component is a movement component caused by a central nervous system disease of the subject. (18) The method according to either one of (16) and (17), wherein the disease is Parkinson's disease or cerebral stroke. (19) The method according to any one of (16) to (18), wherein a frequency range caused by the disease-induced movement component differs from a frequency range resulting from the frequency of the non-disease-induced movement component. (20) The method according to any one of (16) to (19), wherein the frequency range caused by the disease-induced movement component is higher than the frequency range resulting from the frequency of the non-disease-induced movement component. (21) The method according to any one of (16) to (20), wherein the disease-induced movement component is a movement component relevant to involuntary movement of the subject. (22) The method according to any one of (16) to (21), wherein the non-disease-induced movement component is a movement component relevant to voluntary movement of the subject. (23) The method according to any one of (16) to (22), wherein, in the step of analyzing the frequency, the analyzer classifies, evaluates or quantifies the motor function of the subject according to the ratio of the quantity of the disease-induced movement component and the quantity of the non-disease-induced movement component. (24) The method according to any one of (16) to (23), wherein the disease-induced movement component is a movement component caused in voluntary movement of a patient with a central nervous system disease such as a patient with Parkinson's disease. (25) The method according to any one of (16) to (24), wherein the non-disease-induced movement component contains a predicted movement component for moving the cursor image based on the subject's prediction of the movement of the target image, and a feedback movement component for the subject to correct the error between the target image and the cursor image. (26) The method according to (25), wherein, in the step of analyzing the frequency, the analyzer classifies, evaluates or quantifies the motor function of the subject according to the ratio of the quantity of the disease-induced movement component and the quantity of the predicted movement component. (27) The method according to any one of (15) to (26), wherein the frequency analysis is carried out using a Fourier analysis. (28) The method according to (27), wherein the Fourier analysis is a fast Fourier analysis.

Effect of the Invention

The present invention provides a system for evaluating a motor function of a subject with higher accuracy. According to a system or a method of the present invention, the frequency characteristics of a motor function of a subject can be detected in a simple and non-invasive manner by detecting a tracking status of a target image displayed on a display unit tracked by the subject via a cursor image using a moving unit.

EMBODIMENTS FOR CARRYING OUT THE INVENTION

Hereinafter, a motor function analysis system of the present invention and a method for operating the same will be described in more detail. The scope of the present invention is not limited to the following description, and may appropriately be modified and carried out in a way other than the following examples without departing from the scope of the invention.

I. Summary

Figure 4:
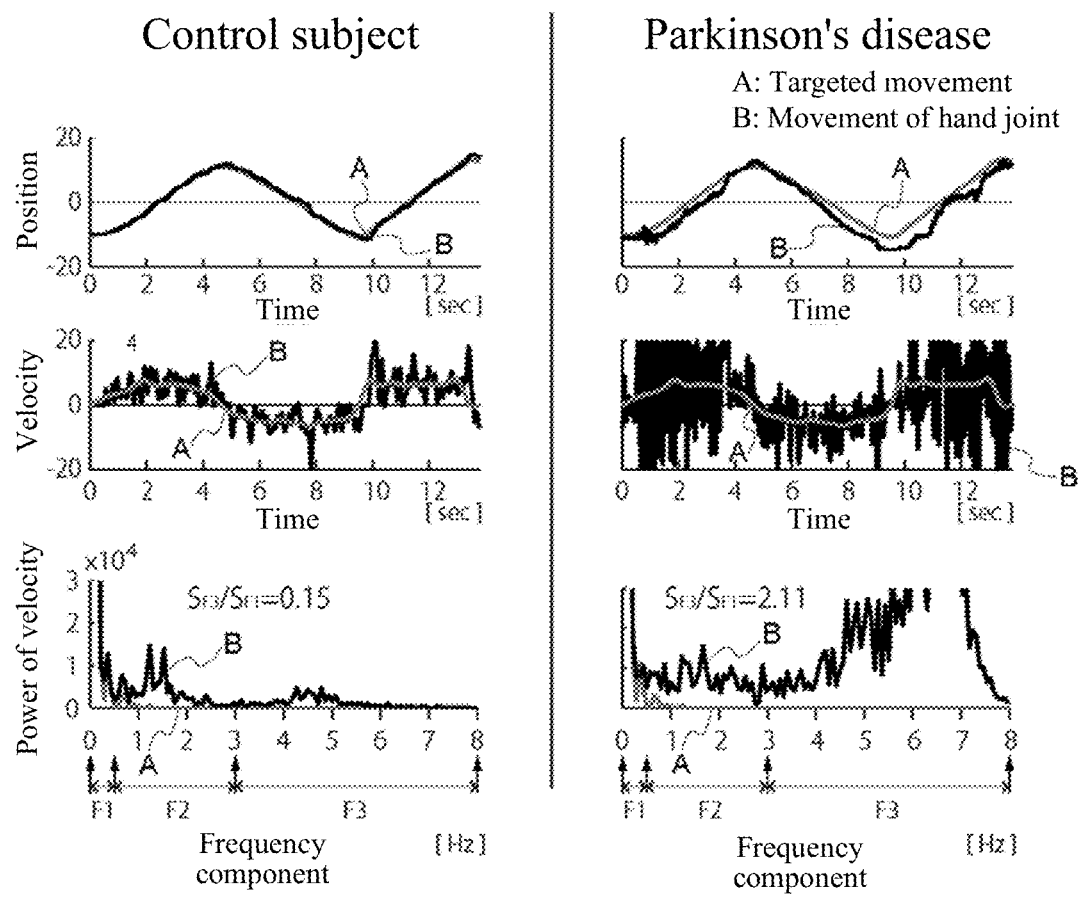
FIG. 4 Diagrams for comparing a movement of a normal control subject and a movement with microsteps of a patient with Parkinson's disease.

The present inventors found that fine stepwise movement or microvibration around 6 Hz (3-8 Hz) can be observed during a visually-guided tracking movement of a patient with Parkinson's disease by using a motor function analysis system described below. This phenomenon has been unknown even to the experts in Parkinson's disease. The present inventors have named this phenomenon microsteps due to the shape of the waveform thereof. The microsteps are extremely weak in normal subjects or patients with cerebellar dysfunction, and it increases specific to central nervous system diseases such as Parkinson's disease. From the past studies by the present inventors, it is known that the motor command for the predictive control that takes part in execution of the tracking movement is included in 0-0.5 Hz while the motor command for the feedback control for correcting the error is included in 0.5-3 Hz. Based on the past studies by the present inventors, the frequency components (predicted movement components) in 0-0.5 Hz are defined as the F1 frequency domain or a first frequency domain (FIG. 4) while the frequency components (feedback movement components) in 0.5-3 Hz are likewise defined as the F2 frequency domain or a second frequency domain (FIG. 4). Meanwhile, microsteps (3-8 Hz) were found to belong to a higher frequency band that is distinctly different from either components, and have different source and functional significance. The frequency components (disease-induced movement components) in 3-8 Hz are newly defined as the F3 frequency domain or a third frequency domain (FIG. 4).

Using this microsteps phenomenon, the present invention proposes simple and non-invasive system and method for making early diagnosis and evaluating a pathological condition of a central nervous system disease such as Parkinson's disease and cerebral stroke with high accuracy, as well as quantitatively evaluating drug therapy for a central nervous system disease such as Parkinson's disease, and evaluating a pathological condition during the process of recovery from movement disorder (mainly hemiplegia) due to cerebral stroke. These system and method perform a frequency analysis of the body movement of a patient (subject) who is undergoing target tracking movement by a fast Fourier analysis. According to these system and method, quantities (powers) of the low-frequency component (F1: 0-0.5 Hz) for the predictive control of the tracking movement and the non-voluntary high-frequency microstep component (F3:3-8 Hz) are determined so as to use the ratio of the microstep component to the low-frequency component as an index for evaluating a pathological condition of a central nervous system disease such as Parkinson's disease or cerebral stroke.

II. Experiments and Analysis Methods

Since microsteps analyzed by the present invention are fine movements, it is important to record the body movement with a high-precision device. Therefore, in order to measure the microsteps, a motor function analysis system that makes use of the hand joint movement, which has been developed by the present inventors, was used. Although this motor function analysis system is related to the motor function evaluating system of Japanese Patent No. 5154558 proposed by the present inventors, unlike this system, it is not provided with an electromyogram measuring device. Hereinafter, a motor function analysis system used with the present invention will be described with reference to FIG. 1.

1. Details of Motor Function Analysis System

Figure 1:
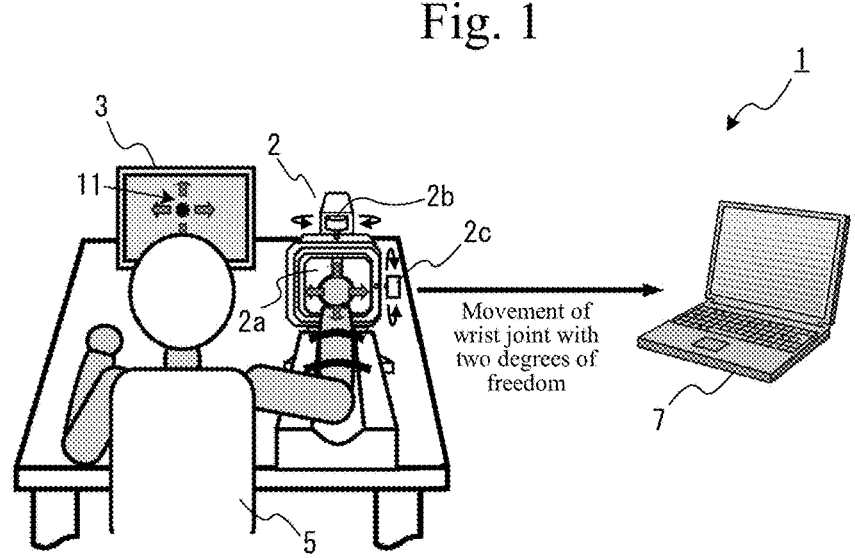
FIG. 1 A conceptual diagram of a motor function analysis system of the present invention.
Figure 2:
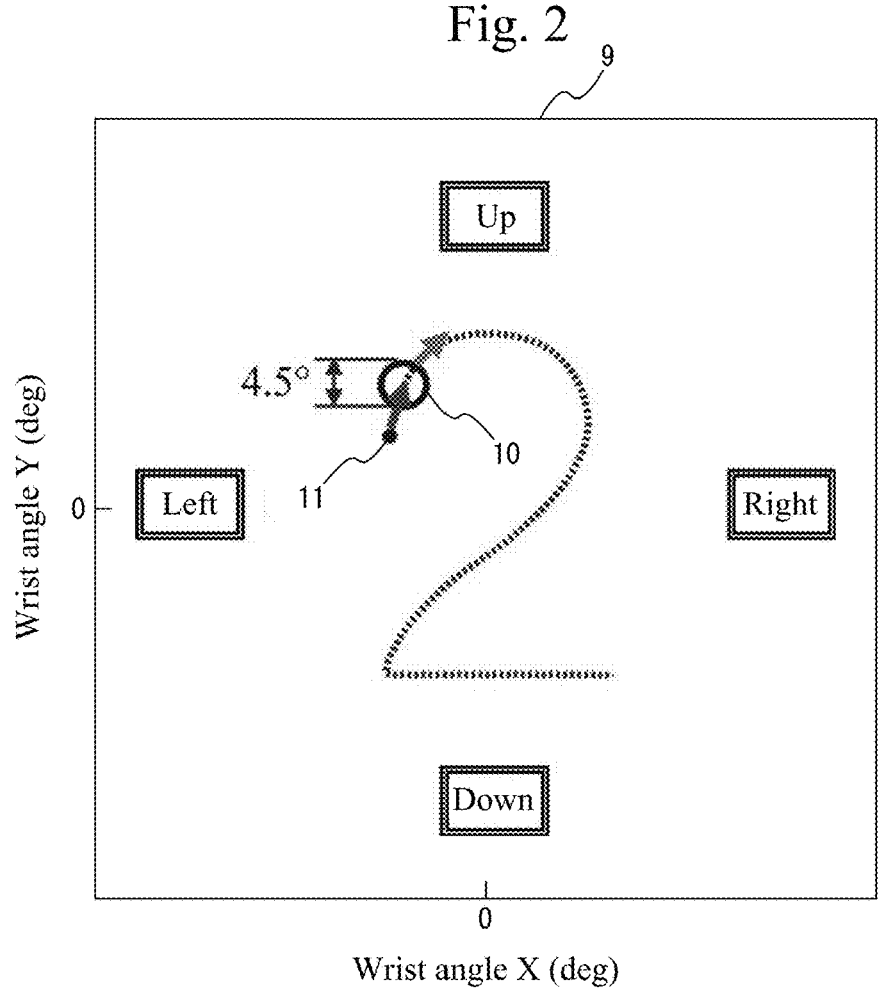
FIG. 2 A view showing an assignment of a hand joint movement given to a subject by the system shown in FIG. 1.

As shown in FIGS. 1 and 2, a motor function analysis system 1 of the present invention (hereinafter, referred to as a system of the present invention) comprises: a display unit 3 for displaying image information 9 including a target image 10 and a cursor image 11 for tracking the target image 10; a tracking unit 2 used by a subject 5 to move the cursor image 11; and an analyzer 7 for processing the result tracked by the tracking unit 2.

The analyzer 7 detects the tracking status of the target image 10 tracked by the cursor image 11 and analyzes this tracking status. Furthermore, the analyzer 7 extracts and evaluates microsteps from the results of analysis. Preferably, the analyzer 7 is a computer.

The system of the present invention may be any system that can evaluate the motor function of a subject. Although the movement site is not limited, it is preferable that the system evaluates, in particular, the motor function of the wrist movement among the various motor functions. The motor function of the wrist movement to be evaluated is preferably a motor function of the wrist joint that has two degrees of freedom, namely, the motor function of the wrist joint in the horizontal direction (X-axis direction; right/left), the vertical direction (Y-axis direction; up/down) as well as the combination thereof (the same applies hereinafter).

Hereinafter, the system of the present invention will be described in detail. Those skilled in the art should be capable of establishing and implementing the system of the present invention for motor functions other than the wrist movement of a subject, in light of the description of the motor function of the wrist movement, the technically common knowledge in this technical field and else.

(1) Display Unit

The display unit 3 of the system of the present invention displays image information including a target image 10 and a cursor image 11 shown in FIG. 2. Preferably, the display unit 3 has a display screen 9 for displaying the image information. Examples of the display screen include color or monochrome display type liquid crystal monitors and cathode-ray tube monitors.

The target image 10 refers to a target image to be tracked by the cursor image 11. Although its shape, size, color hue and activity are not particularly limited, preferable examples include at least one image selected from the group consisting of (i) to (iv) below. Among them, images of (i) to (iii) are more favorable.

(i) An image that moves along a predetermined track or that moves in an arbitrary direction.

(ii) At least two images that are fixedly spaced apart from each other with a predetermined distance.

(iii) A linear image consisting of a straight line and/or a curve with predetermined length and width.

(iv) An image consisting only of a starting point and an end point.

Examples of the predetermined track in the image of (i) include those that include at least one selected from the group consisting of a straight line, a curve, a circle and a polygon. Among the above-mentioned images of (i), a preferable embodiment of a target image that moves along a predetermined track is a target image that traces a line representing, for example, some kind of a character (numbers, etc.) as a predetermined track.

Preferably, target images of the images of (ii) above, for example, have one target image at the center with two or more target images positioned on the concentric circle thereof. Specifically, while the target image positioned at the center is always displayed, the target images on the concentric circle thereof are preferably displayed one by one in order such that when one image is displayed the other image is not displayed and that once the image that has been displayed is no longer displayed one of the remaining images is displayed in turn.

The target images of (i) and (ii) above preferably include at least one shape selected from the group consisting of a circle, an oval, a polygon and a star shape.

Preferable examples of the images of (iii) above include lines representing, for example, some kind of characters (numbers, etc.) having predetermined length and width.

Since the images of (iv) above are not particularly determined except that each of them have a starting point and an end point, the cursor image may be moved as imaged by the subject (according to the image in mind).

(2) Tracking Unit

The tracking unit 2 in the system of the present invention may be used by the subject 5 himself/herself to move the cursor image 11 displayed on the display unit 3. As shown in FIG. 1, the tracking unit 2 is preferably provided with a movable part 2a that is manipulated by the subject 5 in an arbitrary direction, and an output unit for transmitting the movement information of this movable part 2a to the display unit 1 as the information of the movement of the cursor image 11. The information may be transmitted from the output unit either as an analog output or a digital output.

Preferably, the tracking unit 2 is further provided with a horizontal direction sensor 2b and a vertical direction sensor 2c for detecting the movement information of the movable part with respect to a predetermined parameter. Here, the predetermined parameter may be, for example, at least one of the position, the velocity and the torque of a part of the subject's body that is involved in the manipulation of the tracking unit 2.

In a case where the system of the present invention is used to evaluate a motor function of the wrist movement of a subject, the tracking unit 2 used is preferably a wrist joint manipulandum. Preferably, the wrist joint manipulandum is capable of detecting at least one of the position, the velocity and the torque of the wrist joint of the subject. Such a wrist joint manipulandum may be commercially available and, for example, "equipment for measuring position, angle velocity and torque of the wrist joint" manufactured by Hoyo Elemec Co., Ltd. or the like may be used.

(3) Analyzer

The analyzer 7 of the system of the present invention detects the target image 10 tracking status by the cursor image 11 moved with the tracking unit 2. The tracking status detected with the analyzer 7 represents the "movement" of the subject, and used for extracting microsteps through a processing described below.

Although the tracking status to be detected is not limited, examples thereof include: (i) representation of the track (continuous track) of the movement of the cursor image tracking the target image; (ii) representation of the position, the direction of movement and the velocity of the movement of the cursor image tracking the target image in terms of vector per unit time; as well as (iii) representation of the movement of the part of the subject's body itself using the tracking unit. For example, in a case where the system of the present invention is used to evaluate the motor function of the wrist movement, the tracking status described in (iii) above may be records of the manipulation status of the movable part of the wrist joint manipulandum manipulated by the subject and the movement angle of the wrist joint manipulating the movable part, represented by two parameters, namely, in the horizontal direction and the vertical direction.

Moreover, the analyzer 7 analyzes the above-described tracking status. Specifically, the analyzer 7 carries out analysis by quantifying or schematizing (including graphing) the detected data relevant to the tracking status as shown in FIGS. 3-7, respectively. The analyzer may be provided with an apparatus that converts the type of the signal of the data acquired with the tracking unit 2 into a desired type, for example, an A/D interface or the like.

The analyzer 7 may further evaluate the motor function of the subject using the above-described analysis results as an index. The approach of the evaluation with the analyzer 7 is not limited as long as the acquired analysis result is used as an index.

The analyzer 7 may be provided with database or the like that contains a number of previously acquired analysis results (analysis results of the data of the detected tracking status). An acquired analysis result may be compared with such database information so that, for example, the therapeutic potential and a pathological condition of a central nervous system disease (a neurodegenerative disease) associated with a movement disorder can easily be evaluated.

(4) Manipulation of System of the Present Invention

As shown in FIG. 1, the subject 5 sits in front of the display unit 3 of a personal computer displaying a cursor and a target, and places the forearm on a rest so as to manipulate the hand joint manipulandum with hand. The movements of the hand joint with two degrees of freedom (preferably, an angle) are measured with two sensors 2b and 2c and are reflected in the movement of the cursor image 11 (black dot with a diameter of 2 mm) on the display unit 3. The target image 10 is displayed as an open circle as shown in FIG. 2, whose diameter (1 cm) corresponds to 4.5 degrees of the movement of the hand joint and whose position serves as an index of the movement of the hand joint.

(5) Outline of Method for Processing Data by Analyzer

Figure 3:
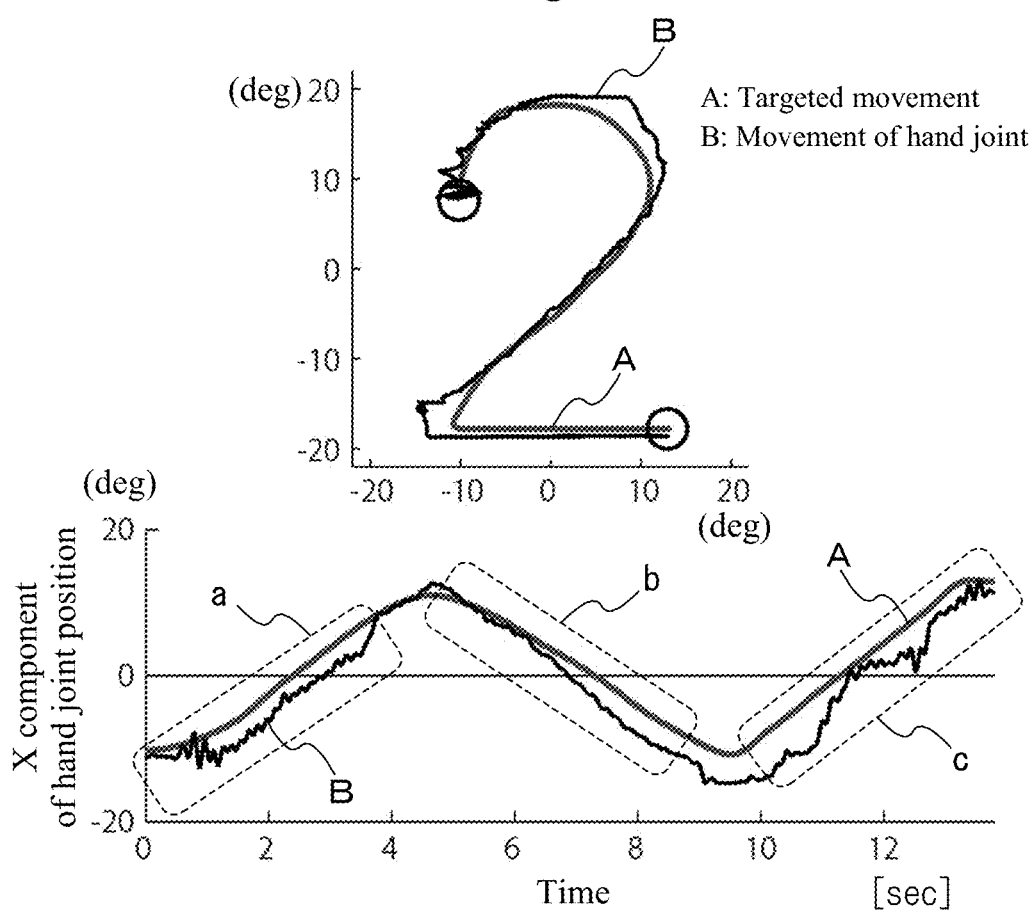
FIG. 3 Views showing the hand joint movement containing typical microsteps of a patient with Parkinson's disease measured by the system shown in FIG. 1.

The analyzer 7 provides data representing the movement (change in angle) of the wrist joint as shown in the upper panel of FIG. 3 based on the tracked result acquired from the tracking unit 2. According to an example of the present invention, the X-direction components (horizontal direction components) of this change in the angle are used for the analysis. As shown in the lower panel of FIG. 3 as well as the upper right and left panels of FIG. 4, the angle of the X component of the wrist joint position changes with time. Although the movement of the wrist joint was exemplified as the "movement" to be analyzed by the analyzer 7, it is not limited thereto, and a movement of other joint such as an ankle or a movement of manipulating the mouse or the like can also be employed. In addition, although the "angle" of the movement was analyzed by the analyzer 7, it is not limited to the angle, and a position, a torque or the like of the movement of the wrist or the like can also be employed.

The lower panel of FIG. 3 as well as the upper right and left panels of FIG. 4 show curve B having fine stepwise microsteps. In order to analyze these microsteps, the X component angles shown in the upper right and left panels of FIG. 4 are differentiated once so as to determine the change rate (velocity) of the angle with time as shown in the middle right and left panels of FIG. 4. This velocity was further subjected to Fourier transform to give the frequency characteristics shown in the lower right and left panels of FIG. 4. Although the process of acquiring the frequency characteristics is preferably fast Fourier transform, it is not limited thereto. The frequency characteristics will be discussed in the following examples in more detail but it was found that, as shown in the lower right panel of FIG. 4, the components that attributed to the microsteps were distributed over the high-frequency domain (3-8 Hz) while the components that attributed to voluntary movement were distributed over the low-frequency domain (0.5-3 Hz).

EXAMPLES

Hereinafter, experiments using the system of the present invention will be described.

III. Subjects and Experimental Assignment

For the experiment, 11 patients with Parkinson's disease, 7 patients with cerebral stroke (6 hemiplegia and 1 cerebellar infarction), and 9 age-matched healthy adults with no history of neurological disease participated as subjects. As an experimental assignment, the subjects were asked to do a hand joint movement for tracking the target image 10 that moves at a constant speed (average speed: 6.2 deg/sec) (FIG. 2). The starting point of the movement was positioned at the upper left part of the display screen 1 (X=−10°, Y=8°). Once a circular target image 10 is displayed at the upper left part of the monitor, the subject moves his/her hand joint to place the coordinating cursor image 11 at the starting point. After 3 seconds, the target image 10 starts to move to draw a track of number "2" at a constant speed. The subject moves the hand joint so as to keep the cursor image 11 within the open circle of the moving target image 10 as much as possible. Each of the subjects were allowed to practice for three times to sufficiently understand the task and underwent the actual runs for 5 times.

In addition to the above-described movement assignment, the resting tremor of the patients with Parkinson's disease that can be observed while resting the cursor image 11 at the center of the screen for 10 seconds were recorded (resting tremor assignment: twice).

IV. Results

During the course of the movement assignment or the resting tremor assignment, the analyzer 7 (computer) records the position (X, Y) of the hand joint, and the velocity of the hand joint was determined by differentiating the respective positional signals once. Moreover, in order to analyze the compositions of the different frequency components contained in the position or the velocity of the hand joint, the analyzer 7 (computer) performed frequency analysis by fast Fourier transform. In the system of the present invention, the microsteps were observed as a movement in a frequency band (3-8 Hz) that is obviously higher than the predictive movement (0.5 Hz or lower) of the subjects or the feedback movement (0.5-3 Hz) of the subjects (see the frequency characteristics shown in the lower right panel of FIG. 4). Thus, the hand joint movements of the subjects were subjected to Fourier transform for a frequency analysis (lower panel of FIG. 4) so that their increases and decreases can be evaluated easily and quantitatively. The examination completes within several minutes, totally non-invasive, with the analysis results being acquired instantly.

1. Frequency Component of Microsteps

FIG. 3 shows a record of a hand joint movement of a right hand of a patient with Parkinson's disease at "Yahr's stage II". Obvious resting tremor was seen with the same right hand of this patient. The term "Yahr's stage" refers to the severity of Parkinson's disease, where "Yahr's stage II" is associated with the second mild degree conditions among the five stages of severity.

The microsteps can be seen almost continuously from the start to the end of the number 2. Since the upper panel of FIG. 3 showing the movement in a two-dimensional diagram is hard to perceive, the lower panel of FIG. 3 shows only the X components of the wrist joint position (angle) with time. As shown in the lower panel of FIG. 3, the microsteps show very fine microsteps (b) or vibration (a, c) within the regions a, b and c surrounded by dashed lines. The presence of this phenomenon can clearly be observed as a waveform that sharply vibrates up and down by differentiating the above-described positions to convert them into velocity representation (see the middle right panel of FIG. 4). The frequency components contained in this velocity waveform obtained by Fourier transform (preferably, fast Fourier transform) are shown in the lower right panel of FIG. 4. According to the movement assignment employed in this experiment, the components of the predictive movement are included in 0-0.5 Hz while the components reflecting the feedback control manipulation by the subject are included in 0.5-3.0 Hz. The components corresponding to the microsteps are mainly distributed over 4-8 Hz which is higher than any of the above components, with the center frequency at approximately 6.5 Hz. The microsteps are obviously components that are totally different from the above-described two components. In contrast, microsteps were scarcely seen or were of an order of magnitude lower in the normal subjects. Hence, the increase in the microstep frequency components in the patients with Parkinson's disease shown in the FIG. 4 represents pathological significance unique to Parkinson's disease.

2. Comparison of Frequencies Between Microsteps and Resting Tremor

Since the frequency band 4-8 Hz representing the microsteps overlaps with the frequency band (typically, about 4-6 Hz) of the resting tremor, i.e., one of the typical conditions of Parkinson's disease, the production mechanisms of them may possibly be at least partially common. Therefore, the same patients having Parkinson's disease shown in FIG. 3 were subjected to a frequency analysis (FIG. 6) with respect to the resting tremor (FIG. 5).

Figure 5:
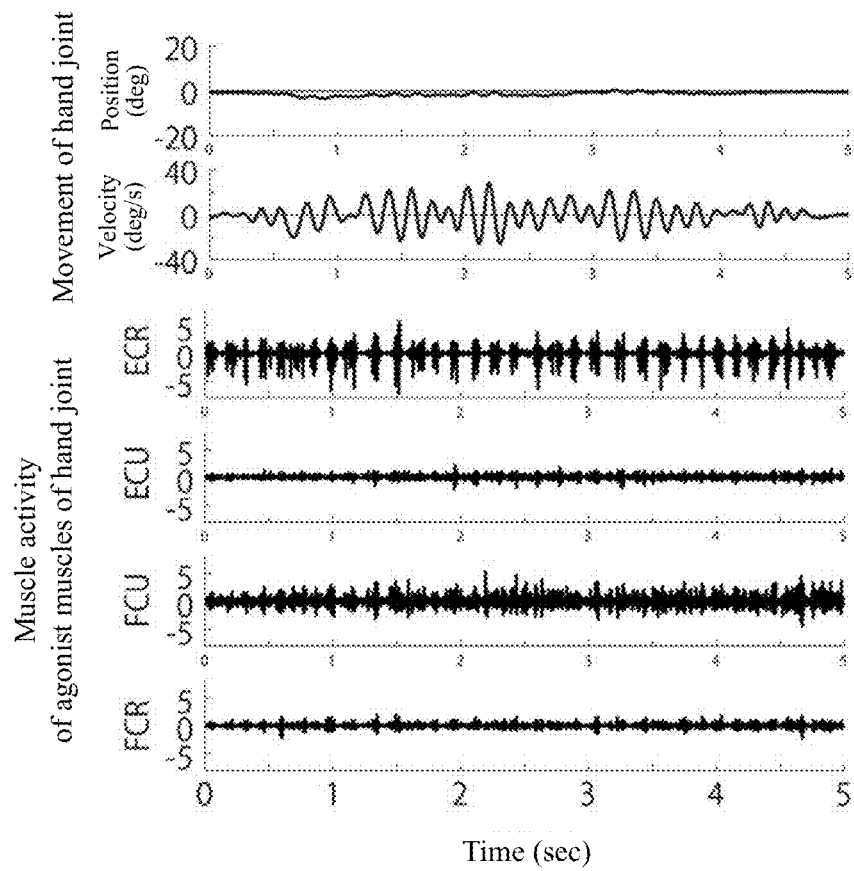
FIG. 5 Diagrams showing resting tremor of the patient with Parkinson's disease shown in FIG. 3.

In addition to the position (first row) and the velocity (second row) of the hand joint in the horizontal direction, FIG. 5 also shows electromyograms of the four agonist muscles of the wrist recorded at the same time (third to sixth rows). The movement of the wrist as well as the muscle action causing the same both show typical patterns of the resting tremor of Parkinson's disease. In FIG. 5, ECR is an electromyogram of the short radial extensor muscle of wrist and long radial extensor muscle of wrist, ECU is an electromyogram of ulnar extensor muscle of wrist, FCU is an electromyogram of ulnar flexor muscle of wrist and FCR is an electromyogram of radial flexor muscle of wrist.

Figure 6:
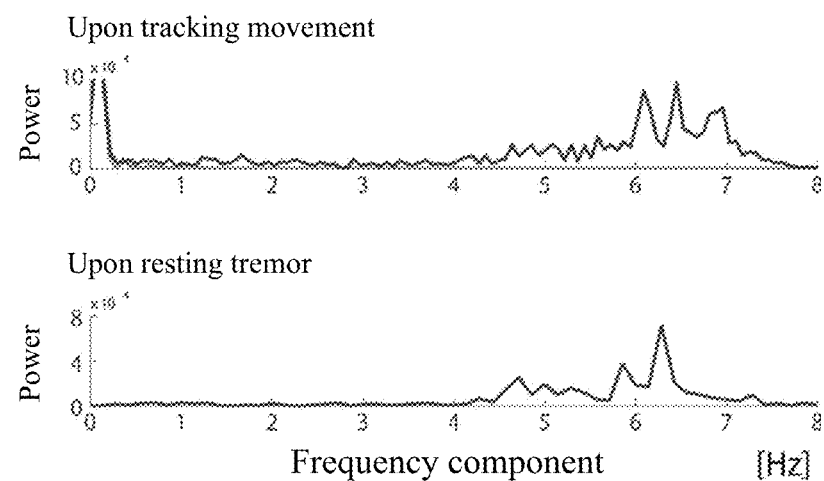
FIG. 6 Diagrams for comparing the frequency distributions between the resting tremor and the tracking movement.

As can be appreciated from FIG. 5, the wrist movements and the muscle actions causing the same of the patients with Parkinson's disease show typical patterns of resting tremor resulting from Parkinson's disease. Thus, the frequency analysis of this resting tremor was performed using the system of the present invention (lower panel of FIG. 6), and the frequency distribution was compared with the frequency analysis of the tracked movement (upper panel of FIG. 6) at the same scale. As shown in FIG. 6, the frequency distribution of the resting tremor was mostly 4.5-7 Hz, which almost matched the frequency distribution of the microsteps of the tracking movement, i.e., 4.5-7.5 Hz. Accordingly, their production mechanisms seemed to be generally common.

Figure 7:
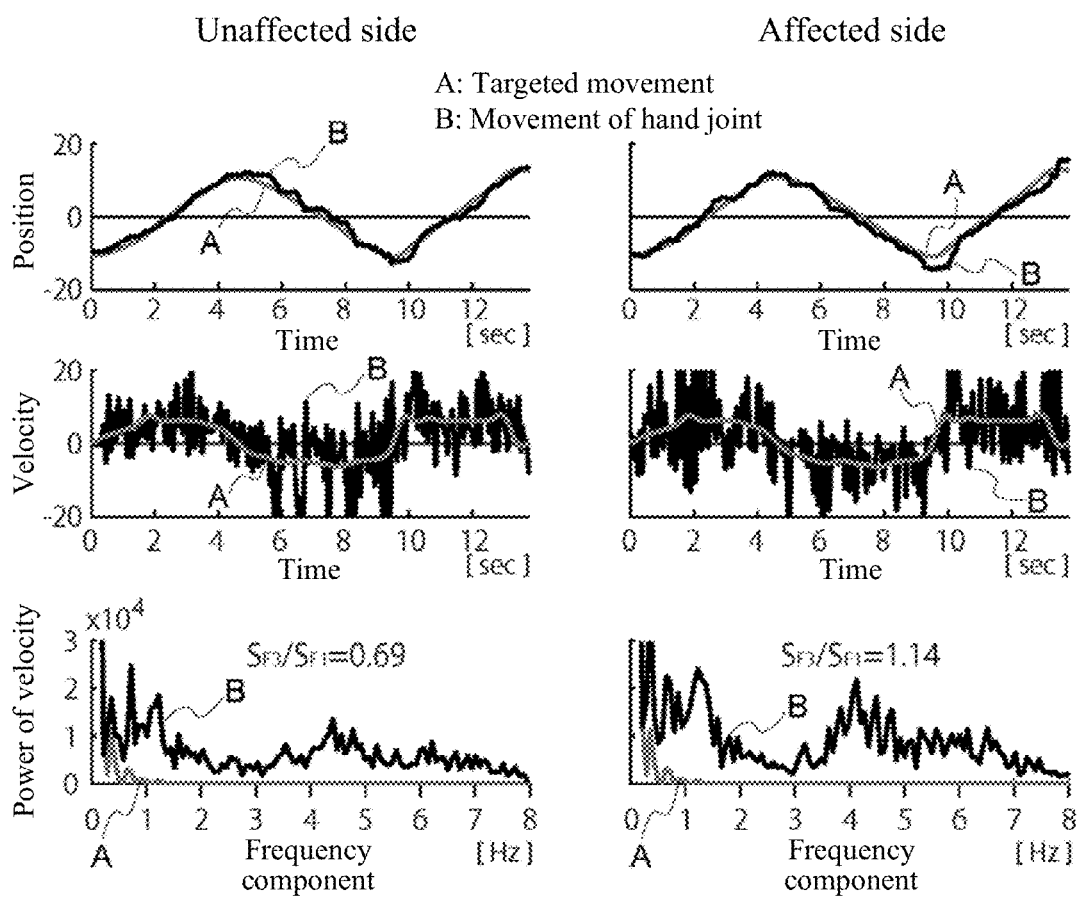
FIG. 7 Diagrams showing microsteps of the unaffected side (left) and the affected side (right) of a patient with unilateral Parkinson's disease.

3. Microsteps at "Unaffected Side" of Patient with Unilateral Parkinson's Disease Parkinson's disease unilaterally occurs at either right or left side, which gradually progresses to the other side. The early stage where the symptoms remains unilaterally is called "Yahr's stage I". FIG. 7 shows data of the unaffected side (left) and the affected side (right) of one exemplary patient at Yahr's stage I. Here, the term "unaffected" means that the three principal features of Parkinson's disease, namely, "tremor, rigidity and akinesia", are not observed upon a clinical examination by an expert. Meanwhile, resting tremor is observed at the affected side on the other side. On the unaffected side (left) of the case shown in FIG. 7, the microsteps are clearly increasing as compared to a normal subject (FIG. 4, left) although not to the extent of that in the affected side on the other side. Accordingly, microsteps can strongly be suggested of their possibility to be used as a highly sensitive diagnostic index that precede the major signs of Parkinson's disease.

4. Quantification of Microsteps During Movement

The analyzer 7 (computer) of the system of the present invention evaluates microsteps by utilizing the frequency components of the patient with Parkinson's disease shown in the lower right panel of FIG. 4. Specifically, referring to the lower right panel of FIG. 4, integrated value $S_{F1}$ of the low-frequency side (quantity of the predicted movement components as the non-disease-induced movement components) is obtained by integrating the low frequency domain of 0-0.5 Hz representing the voluntary predictive control manipulation and integrated value $S_{F3}$ of the high-frequency side (quantity of the disease-induced movement components) is obtained by integrating the high-frequency domain of 3-8 Hz representing the microsteps. Then, the ratio of the high-frequency side integrated value $S_{F3}$ to the low-frequency side integrated value $S_{F1}$ ($S_{F3}/S_{F1}$) is determined. Using this ratio as an index, a pathological condition of Parkinson's disease can be evaluated. Specifically, this ratio can be used as an index indicating the sign of the onset of the early stage of Parkinson's disease or as an index for classifying severity of Parkinson's disease. For example, whereas $S_{F3}/S_{F1}$ was 0.15 for the control subject shown at the left hand side of FIG. 4, $S_{F3}/S_{F1}$ was 2.11 for the patient with advanced Parkinson's disease shown at the right hand side of FIG. 4, which shows an increase by 14 times. Meanwhile, in the case of the patient at an early stage of onset shown in FIG. 7, $S_{F3}/S_{F1}$ was 1.14 (7.6 times) at the affected side (right) while $S_{F3}/S_{F1}$ was 0.69 (4.6 times) at the unaffected side (left), showing significant increase even on the unaffected side compared to the normal case. In such a manner, this index $S_{F3}/S_{F1}$ allows quantitative evaluation of a pathological condition of Parkinson's disease which has conventionally been impossible.

Figure 8:
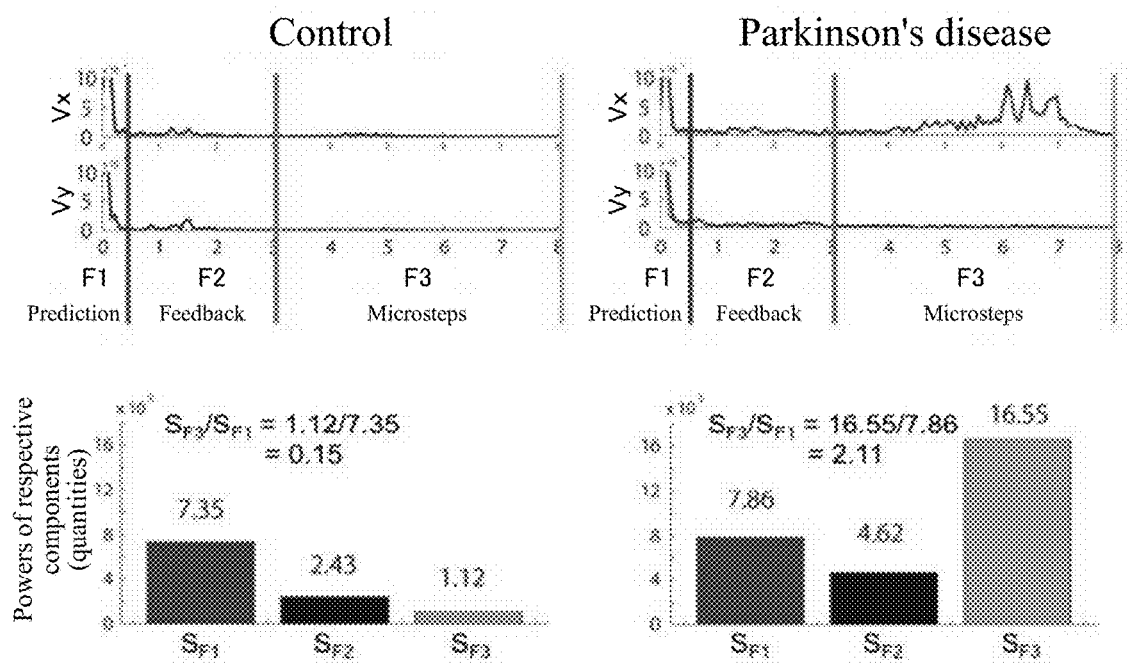
FIG. 8 Diagrams showing a method for quantitatively evaluating the microsteps.

Accordingly, the microstep phenomenon is found to be useful as an index of a pathological condition of Parkinson's disease. In order to make use of it as an index, the microsteps need to be quantified. Thus, the quantification method established by the present inventors will be once again described with reference to FIG. 8. The left panels of FIG. 8 show values of a control subject while the right panels of FIG. 8 show values of a patient with Parkinson's disease. The upper panels of FIG. 8 show frequency analyses of the X components (Vx) and the Y components (Vy) of the movement velocity. The lower panels of FIG. 8 show sums ($S_{F1}$, $S_{F2}$ and $S_{F3}$) of the quantities of the F1 components (0-0.5 Hz), the F2 components (0.5-3.0 Hz) and the F3 components (3.0-8.0 Hz) (power: correlates with the area of the graph) in bar charts, respectively. Vx in the upper panel of FIG. 8 is the same data as that shown in the lower panel of FIG. 4 except note that the scale along the vertical axis and thus the appearance are different. The most significant difference between the control subject and the patient with Parkinson's disease is $S_{F3}$, which is 1.12 for the control while 16.55 for the patient with Parkinson's disease, showing a significant increase by about 15 times.

Figure 9:
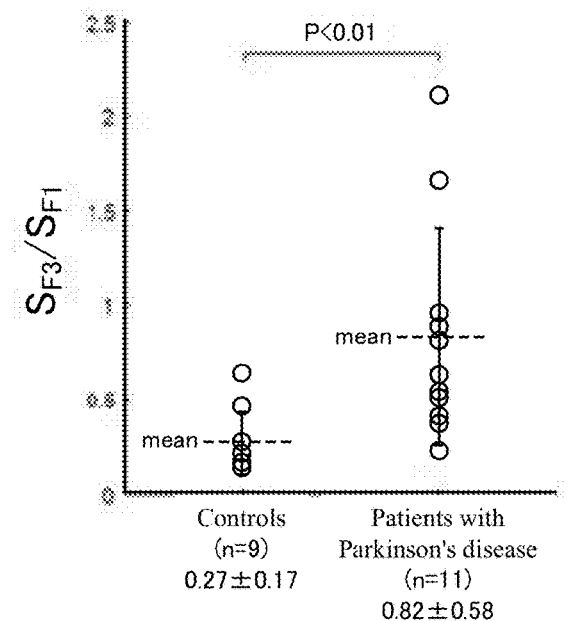
FIG. 9 Diagrams for comparing indexes $S_{F3}/S_{F1}$ between Parkinson's disease and control.
Figure 9:
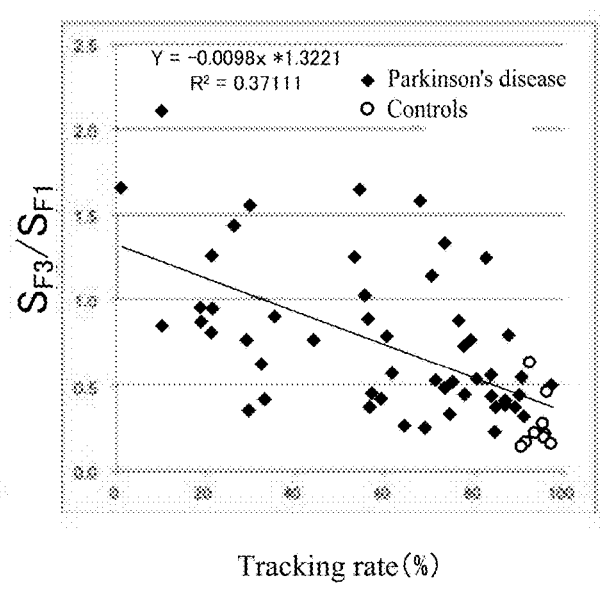

$S_{F3}$ (power) may be sufficient for quantitative comparison but in order to add functional significance, evaluation was carried out using the ratio to the $S_{F1}$ components. The $S_{F1}$ components reflect quantity of the predictive motor command while the $S_{F3}$ components are thought to reflect the quantity of the involuntary noise movement components (see "Discussion"). Therefore, $S_{F3}/S_{F1}$ ratio can be determined to obtain the noise-to-signal ratio (note that the numerator and the denominator of this ratio are opposite from those of a signal-to-noise ratio used in information engineering). When $S_{F3}/S_{F1}$ were calculated for the two examples shown in FIG. 8 (lower panels of FIG. 8), $S_{F3}/S_{F1}$ was 0.15 for the control while it was 2.11 for the patient. From these results, the involuntary noise is caused twice as much as the voluntary movement in the patient, suggesting that the control is inefficient. When $S_{F3}/S_{F1}$ were calculated for 9 normal subjects and 11 patients with Parkinson's disease, $S_{F3}/S_{F1}$ were 0.27±0.17 for the normal subjects while they were 0.82±0.58 for the patients with Parkinson's disease, showing apparent significant difference (p<0.01) (FIG. 9, left). Furthermore, negative correlation was found between $S_{F3}/S_{F1}$ and the accuracy of tracking (tracking rate (%): which indicates how much % of the time the cursor was kept within the target circle during a single run) (FIG. 9, right), showing that the precision of the movement was poorer at higher $S_{F3}/S_{F1}$. This suggested that the F3 components functionally serve as something like noise.

5. Decrease in Microsteps Owing to Drug Therapy for Parkinson's Disease

Figure 10:
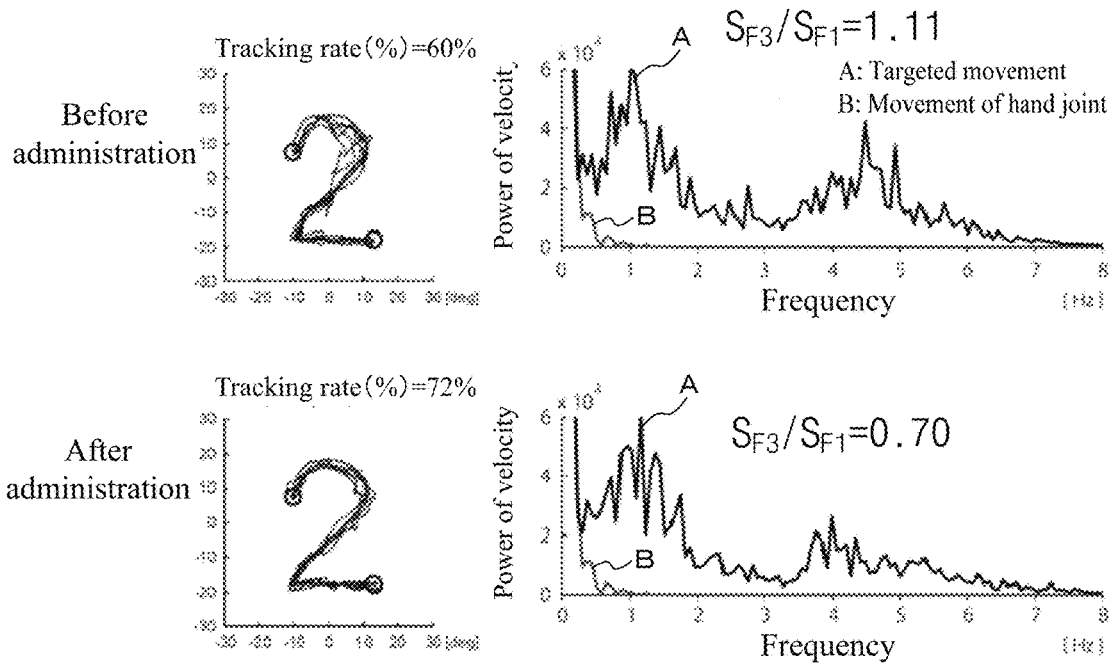
FIG. 10 Diagrams showing evaluation of the therapeutic effect of L-DOPA according to indexes $S_{F3}/S_{F1}$.

For almost all of the patients with Parkinson's disease, drug therapy is performed in which the brain dopamine lacking in the patients is symptomatically supplemented through internal use of levodopa (L-DOPA: L-3, 4-dihydroxyphenylalanine). Its therapeutic effect is often evaluated by "Unified Parkinson's Disease Rating Scale (UPDRS)". Although this scale allows very detailed evaluation as compared to the Yhar's severity classification, it scores severity into four stages for various subscales, which is not quantitative and thus subjective judgment of the physician cannot be omitted. Additionally, it is time taking to examine various subscales which is not suitable since a great burden is borne on both the patient and the physician for frequently repeated evaluations. Therefore, the possibility of using $S_{F3}/S_{F1}$ index to simply quantify the effect of L-DOPA in a patient with Parkinson's disease was examined (FIG. 10). This case was a man in his sixties who was untreated at the initial visit. He was diagnosed to be affected only on one side and thus Yhar's severity classification was at the mildest stage I.

Although it was a relatively mild case before the treatment, the tracking of the movement showed increase in the fine jagged parts and lacked smoothness (FIG. 10, left), suggesting an increase in the microsteps. In fact, $S_{F3}/S_{F1}$ was 1.11 at this point, confirming significant increase of the microsteps (FIG. 10, upper right panel). After administration of the drug, both of the track smoothness and the tracking rate improved (from 60% to 72%), and the microsteps decreased to $S_{F3}/S_{F1}$=0.7. UPDRS evaluation was performed before and after this drug administration. The score improved from 25 to 14 upon evaluation of only Part 3 (motor function), showing that $S_{F3}/S_{F1}$ had good correlation with clinical evaluation.

Figure 11:
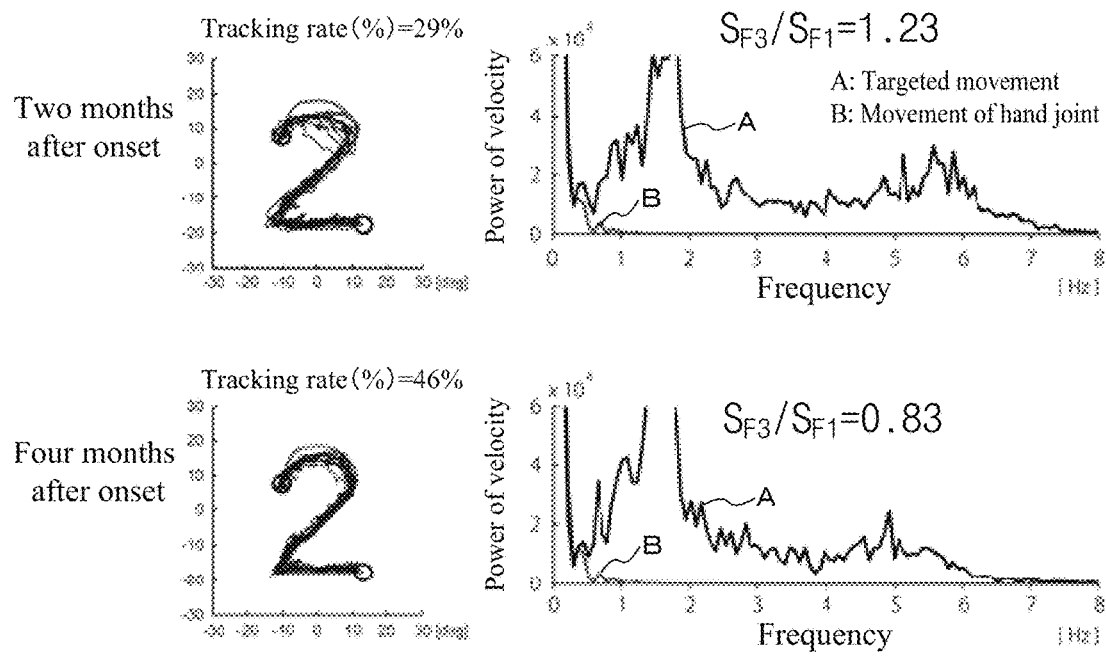
FIG. 11 Diagrams showing evaluation of the therapeutic effect after the incidence of cerebral stroke according to indexes $S_{F3}/S_{F1}$.

6. Increase in Microsteps after Incidence of Cerebral Stroke and Decrease During Process of Recovery In Parkinson's disease, the muscle tension and the stretch reflex are known to increase. Meanwhile, in cerebral stroke, particularly the most frequently occurring hemiplegia, the muscle tension of the flexor muscles and the stretch reflex are known to increase as well. Accordingly, some kind of common pathological condition seems to exist between the two diseases, suggesting the possibility of use of the microsteps as a pathological condition index for patients with cerebral stroke. Thus, 7 patients with cerebral stroke (6 hemiplegia and 1 cerebellar infarction) were asked to participate the same movement assignment of tracking the number 2 and the quantities of the microsteps were evaluated as $S_{F3}/S_{F1}$ ratio (FIG. 11 shows a typical example). This case corresponds to D in FIG. 12. Records after 2 months (upper panel) and 4 months (lower panel) following the incidence are shown. On 2nd month, the track often greatly deviated from the target with the $S_{F3}/S_{F1}$ ratio being as high as 1.23. Thereafter, rehabilitation treatment was continued and after another 2 months (4 months after the incidence), the track became closer to the target with increased smoothness and the $S_{F3}/S_{F1}$ ratio improved to 0.83.

Figure 12:
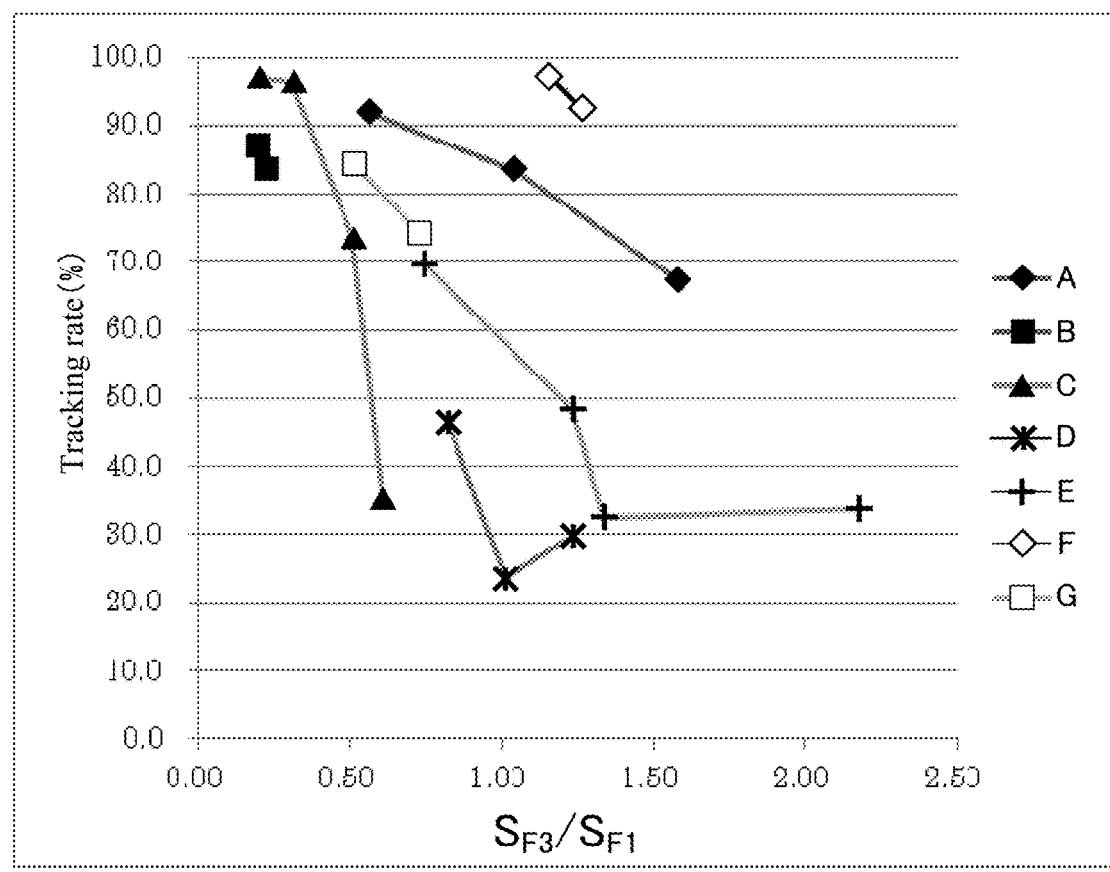
FIG. 12 A diagram showing the relationship between the indexes $S_{F3}/S_{F1}$ and the tracking rates of patients with cerebral stroke.

Moreover, in the 6 cases of patients with cerebral stroke analyzed this time, 2-4 times of records were repeated at generally monthly intervals to analyze the change in the relationship between the motor function (tracking rate) and the $S_{F3}/S_{F1}$ ratio with time (FIG. 12). As a result, negative correlation was found between $S_{F3}/S_{F1}$ and tracking rate similarly in the patients with cerebral stroke, where the $S_{F3}/S_{F1}$ ratio decreased with the recovery of the motor function.

V. Discussion

1. Functional Significance of Microsteps

In the experiment system used by the present inventors, the components of predictive control for the target tracking movement are contained in 0-0.5 Hz while the components of feedback control are contained in 0.5-3.0 Hz. Therefore, the components of 3-8 Hz that correspond to the microsteps are considered to be distinguished from and thus functionally different from either components. Although correspondence with a particular function cannot be decided at this point, there could be a leading hypothesis as will be described below.

In a patient with Parkinson's disease, the stretch reflex (monosynaptic reflex) and the reflex gain thereof are known to be increased. Since the stretch reflex has a negative feedback action and has functions of cancelling disturbance and maintaining the posture, it will interfere with the function of the motor command upon voluntary movement of the body. Thus, in order to allow smooth voluntary movement, the stretch reflex is preferably suppressed in advance. In fact, the stretch reflex is known to be suppressed upon voluntary movement by a normal subject. Since the stretch reflex is in an increased state in Parkinson's disease, suppression of the stretch reflex upon voluntary movement will be insufficient, where the stretch reflex would interfere with the voluntary movement. This is not so strong as to halt the movement, but presumed to manifest as microstep phenomenon with lack of smoothness. As a machine without lubrication would squeak, microsteps are a phenomenon of so to say a "squeak" that appears in muscle action. Since microsteps can also be seen in the unaffected side of the Parkinson's disease, the increase thereof would mean that the state is one step ahead of full-blown movement disorder. In this regard, microsteps is surely a pathological phenomenon. This interpretation was also supported by the data that was newly shown this time, that microsteps also increased in the case of cerebral stroke, which has a different cause of illness from Parkinson's disease but shows increases in the muscle tension and the stretch reflex similar to those of Parkinson's disease, which decreased along with the improvement in the pathological conditions (FIGS. 11 and 12).

2. Relationship Between Resting Tremor and Microsteps, and Microsteps as Preceding Index of Parkinson's Disease Among the symptoms of Parkinson's disease, "resting tremor" is famous, which is one of the three principal features (tremor, rigidity and akinesia) of Parkinson's disease. Resting tremor is typically about 4-6 Hz, which, as the name suggests, appears during rest and disappears upon active movement. Therefore, it may differ from the microsteps that appear during the active movement. According to the studies by the present inventors this time, however, since the microsteps and the resting tremor had almost the same frequency components in the same hand joint of the same patient, there is a high possibility that their production mechanisms are quite common to each other. Meanwhile, since only microsteps and not resting tremor are observed on the unaffected side of a patient with unilateral Parkinson's disease, microsteps are considered as a preceding phenomenon of resting tremor. Summing up these two observations, although resting tremor had been thought to "disappear" upon voluntary movement, in fact it is highly possible that the intensity thereof is only greatly attenuated and continues to remain as microsteps during the voluntary movement. Briefly, both of them are considered to be the same phenomenon but only with different manifestations and may shift from one another. Accordingly, microsteps can be regarded as an early diagnosis index of Parkinson's disease. If so, there may be two psychological reasons that even the experts who routinely diagnose Parkinson's disease have not realized about the microsteps. One reason is that the fine movements in a movement were difficult to be recognized without a special dynamic vision. Second reason is that the fine microsteps have been masked by the very noticeable resting tremor.

3. Application of Microsteps

Over about 200 years since J. Parkinson has first described about Parkinson's disease in 1817, microsteps have been a phenomenon that was unrecognized upon clinical examinations by physicians. Microsteps are valuable as an exquisite index for analyzing a pathological condition of Parkinson's disease and cerebral stroke. Taking advantage of this exquisite feature, there are at least three clinical applications as described below.

a) Early Diagnosis Index of Parkinson's Disease:

As already described in the discussion, microsteps are considered to be utilized as an early diagnosis index of Parkinson's disease. For further proof, studies involving comparison of frequencies between microsteps and resting tremor upon progression of the pathological condition in the "unaffected side" of an unilateral patient that leads to "onset" presenting resting tremor, are in progress.

b) Judgment of Drug's Therapeutic Effect for Parkinson's Disease (Future Assignment):

In the currently most standard treatment of Parkinson's disease, levodopa (L-DOPA) is internally administered for treatment. Although levodopa has an extremely high effect for sometimes after the start of administration, the effect gradually reduces as the administration period becomes longer, which requires increased dose and so-called "off" state starts to appear with shorter duration of effectiveness. Incidence of off period is unstable, during which the movement of the body becomes hard all of a sudden. It causes a great deal of difficulty if this occurs outside of the house and therefore the patient would avoid going out, resulting in severe impairment in Quality Of Life (QOL). Additional internal use of levodopa before the off state may help but currently there is no objective way of knowing the timing. If a premonitory phenomenon of off state can be detected, one would know the timing for taking the drug, which may have a great chance of greatly improving the patient's QOL. Microsteps could be an exquisite index for reflecting a pathological condition of Parkinson's disease and a preceding index of off state. An increase in the microsteps as a premonitory phenomenon of off state is currently searched.

Here, if levodopa treatment can be evaluated, it may also be applicable to evaluation of the effects of other treatment methods for Parkinson's disease such as deep brain stimulation treatment and a soon-to-be available treatment associated with transplantation of dopaminergic neurons derived from iPS cells.

c) Application as Recovery Index of Cerebral Stroke:

As have been shown this time, similar to Parkinson's disease, microsteps were also found to increase in a patient with cerebral stroke with increased muscle tension and stretch reflex. Similar to Parkinson's disease, the increase in the microsteps and the decrease in the motor function had negative correlation. In the patients with cerebral stroke, the motor function improved and the microsteps decreased through rehabilitation. As a result, microsteps are expected to play a role as an evidence for quantitatively evaluating rehabilitation, which has strongly been desired. Since it can be employed for any type of rehabilitation, it is not only suitable for general rehabilitation carried out by occupational therapists or physical therapists but also for precisely evaluating the latest rehabilitation using the front-line therapy such as repetitive transcranial magnetic stimulation therapy and botox therapy.

DESCRIPTION OF REFERENCE NUMERALS

1 Motor function analysis system
2 Tracking unit (wrist joint manipulandum)
2a Movable part
2b Horizontal (X) direction sensor
2c Vertical (Y) direction sensor
3 Display unit
5 Subject
7 Analyzer
10 Target image
11 Cursor image

The invention claimed is:

1. A motor function analysis system for analyzing a motor function of a subject and making disease determination and evaluation about the subject based on the motor function analysis, said system comprising:
   a display unit for displaying image information including a moving target image and a cursor image for tracking said target image;
   a tracking unit in communication with the display unit, wherein the subject moves the cursor image on the display unit with the tracking unit when tracking the moving target image, the tracking unit including a sensor detecting at least one of a position, a velocity and a torque of a part of the subject that is involved in manipulating the tracking unit; and
   a computer having a display in communication with the display unit and the tracking unit,
   wherein the computer detects and graphs on the display a tracking status of the target image tracked by the cursor image on the display and determines a frequency of movement components contained in the tracking status,
   wherein the computer separates a first frequency domain relating to a predicted movement component, a second frequency domain relating to a feedback movement component, which is higher than the first frequency domain, and a third frequency domain relating to a disease-induced movement component, which is higher than the second frequency domain, from the frequency of movement components, and wherein the computer determines a quantitative diagnostic index regarding a motor function of the subject according to a ratio of a quantity of the disease-induced movement component obtained from an integrated value of the third frequency domain and a quantity of the predicted movement component obtained from an integrated value of the first frequency domain, and
   wherein the quantitative diagnostic index is used to make disease determination and evaluation about the subject.

2. The system according to claim 1, wherein the disease-induced movement component is a movement component caused by a central nervous system disease of the subject.

3. The system according to claim 2, wherein the disease is Parkinson's disease or cerebral stroke.

4. The system according to claim 1, wherein the disease-induced movement component is a movement component relevant to involuntary movement of the subject.

5. The system according to claim 1, wherein the predicted movement component is a movement component relevant to voluntary movement of the subject.

6. The system according to claim 1, wherein the disease-induced movement component is a movement component caused in voluntary movement of a patient with a central nervous system disease.

7. The system according to claim 1, wherein the predicted movement component is used for moving the cursor image based on the subject's prediction of the movement of the target image, and the feedback movement component for the subject is used to correct an error between the target image and the cursor image.

8. The system according to claim 1, wherein the frequency determination is carried out using a Fourier analysis.

9. The system according to claim 8, wherein the Fourier analysis is a fast Fourier analysis.

10. A method for operating a motor function analysis system for analyzing a motor function of a subject and making disease determination and evaluation about the subject based on the motor function analysis, said method comprising the steps of:
    displaying image information including a moving target image and a cursor image for tracking the target image on a display unit;
    moving the cursor image on the display unit with a tracking unit manipulated by the subject, the tracking unit including a sensor detecting at least one of the position, the velocity and the torque of a part of the subject that is involved in manipulating the tracking unit; and
    detecting a tracking status of the target image tracked by the cursor image on the display unit and analyzing a frequency of a movement component contained in the tracking status with a computer,
    wherein, in the step for analyzing the frequency, the computer separates a first frequency domain relating to a predicted movement component, a second frequency domain relating to a feedback movement component, which is higher than the first frequency domain, and a third frequency domain relating to a disease-induced movement component, which is higher than the second frequency domain, from the frequency of movement components, and wherein, in the step of analyzing the frequency, the computer determines a quantitative diagnostic index regarding the motor function of the subject according to a ratio of a quantity of the disease-induced movement component obtained from an integrated value of the third frequency domain and a quantity of the predicted movement component obtained from an integrated value of the first frequency domain, and using the quantitative diagnostic index to make disease determination and evaluation about the subject.

11. The method according to claim 10, wherein the disease-induced movement component is a movement component caused by a central nervous system disease of the subject.

12. The method according to claim 11, wherein the disease is Parkinson's disease or cerebral stroke.

13. The method according to claim 10, wherein the disease-induced movement component is a movement component relevant to involuntary movement of the subject.

14. The method according to claim 10, wherein the predicted movement component is a movement component relevant to voluntary movement of the subject.

15. The method according to claim 10, wherein the disease-induced movement component is a movement component caused in voluntary movement of a patient with a central nervous system disease.

16. The method according to claim 10, wherein the predicted movement component is used for moving the cursor image based on the subject's prediction of the movement of the target image, and the feedback movement component for the subject is used to correct the error between the target image and the cursor image.

17. The method according to claim 10, wherein the frequency analysis is carried out using a Fourier analysis.

18. The method according to claim 17, wherein the Fourier analysis is a fast Fourier analysis.

* * * * *